United States Patent [19]

Flugstad et al.

[11] Patent Number: 5,384,544
[45] Date of Patent: Jan. 24, 1995

[54] METHOD AND APPARATUS FOR CALIBRATING THE ENERGY OUTPUT OF A DEFIBRILLATOR

[75] Inventors: Ben Flugstad, McMinnville; Judith Cyrus, Newberg; Daniel J. Powers, McMinnville, all of Oreg.

[73] Assignee: Hewlett-Packard Corporation, Palo Alto, Calif.

[21] Appl. No.: 25,295

[22] Filed: Mar. 2, 1993

[51] Int. Cl.⁶ .................... G01R 27/26; G01R 35/00; A61N 1/39
[52] U.S. Cl. .................... 324/678; 324/601; 324/659; 607/8; 364/481
[58] Field of Search .............. 324/548, 601, 659, 677, 324/678, 686; 320/1; 607/5, 8, 11; 364/481, 483

[56] References Cited

U.S. PATENT DOCUMENTS

| | | | |
|---|---|---|---|
| 5,146,412 | 9/1992 | Jones | 324/678 X |
| 5,222,480 | 6/1993 | Couche et al. | 607/5 |
| 5,237,989 | 8/1993 | Morgan et al. | 607/5 |
| 5,245,294 | 9/1993 | Kumar | 324/678 X |

*Primary Examiner*—Gerard R. Strecker
*Assistant Examiner*—Diep Do
*Attorney, Agent, or Firm*—Brent F. Logan; Curtis G. Rose

[57] ABSTRACT

A defibfillator has a self healing storage capacitor connected in parallel with a safety resistor, and a microcontroller. Upon receipt of a calibration request, the microcontroller charges the capacitor to a charging voltage greater than a starting voltage, then discharges the capacitor through the safety resistor. As the capacitor is discharging, the microcontroller continuously measures the voltage across the capacitor. When the microcontroller detects that the voltage across the capacitor is less than or equal to a starting voltage, a timer in the microcontroller is started. When the microcontroller detects that the voltage across the capacitor is less than or equal to an ending voltage, the timer in the microcontroller is stopped. The microcontroller then determines an elapsed time between the time the timer was started and stopped. The microcontroller then calculates a capacitance value of the capacitor based on the starting voltage, the ending voltage, and the elapsed time. This capacitance value is stored in memory, and used to calibrate the energy output of the defibrillator by assuring that the self healing storage capacitor has been charged to a voltage level sufficient to deliver the desired amount of energy to a patient.

8 Claims, 4 Drawing Sheets

METHOD AND APPARATUS FOR CALIBRATING THE ENERGY OUTPUT OF A DEFIBRILLATOR

BACKGROUND

Defibrillators are used to supply a large amount of electrical energy to a patient through paddles. Prior to delivery, this energy is accumulated on a high-voltage capacitor. The amount of energy supplied to the patient is a predetermined value, selected as appropriate for the patient.

Defibrillators typically measure the voltage across the high-voltage capacitor and calculate the energy accumulated on it according to the following equation, where E is energy, C is the capacitance of the capacitor, and V is the voltage across the capacitor:

$$E = \tfrac{1}{2}CV^2. \tag{1}$$

Ideally, in determining the appropriate voltage for a desired energy, the capacitor's actual capacitance is used rather than its nominal value because any variance between in the capacitance value used and its actual value results in a corresponding error in the amount of energy delivered to the patient. For example, if the actual capacitance is five percent less than the value used to determine voltage, then the energy supplied to the patient will also be five percent less than intended.

A capacitor's actual capacitance can differ from its nominal value for many reasons. The difference could be due to manufacturing variations. However, such variations could be detected and accounted for during manufacture of the defibrillator.

Just as important are changes in the capacitance which occur after the defibrillator leaves the factory. For example, some capacitors lose capacitance as they age. Also, high-voltage metalized film capacitors or paper capacitors can lose capacitance when charged to voltages near their maximum rated voltages, a situation common in defibrillators. The dielectric material separating the metal layers can break down, allowing a localized arc. Although the dielectric material is destroyed at this location by the arc, the metalization at the location also evaporates from the heat of the arc, thereby maintaining the operational integrity of the capacitor. This type of capacitor is known as a self healing capacitor. However, this small reduction in capacitor plate area decreases the capacitance by a corresponding amount. This effect is cumulative over the life of the capacitor, and may decrease the capacitance by more than five percent.

For the foregoing reasons, there is a need for a defibrillator which can determine the actual capacitance of its storage capacitor, and store the value for future energy calculations. To adequately satisfy this need, the defibrillator should be able to calibrate its capacitor as needed throughout the life of the defibrillator.

SUMMARY

The present invention is directed to a method that satisfies this need of calibrating a defibrillator's storage capacitor, and does so without requiring the defibrillator to contain any more components than are normally present.

The method of the present invention uses the safety resistor and safety relay already present in a defibrillator to measure and calibrate the defibrillator's storage capacitor. The safety resistor has a known resistance R and is connected in series with the safety relay across the capacitor. The defibrillator also has a means for measuring the capacitor's voltage and a timer.

With the safety relay open circuited, the storage capacitor is charged to a starting voltage $V_0$. The safety relay is then closed, initiating the disarm of energy from the capacitor into the safety resistor. The capacitor voltage is compared against an ending voltage $V_1$, which is less than the starting voltage $V_0$. The amount of time which elapses between when the capacitor voltage is the starting voltage $V_0$ and the ending voltage $V_1$ is measured. The capacitance C of the storage capacitor is then determined according to the equation $$C = \frac{t}{R(\ln(V_0/V_1))}. \tag{2}$$

Since the resistance R of the safety resistor is known and the starting and ending voltages $V_0$ and $V_1$ can be predetermined, the capacitance C can be determined by multiplying the elapsed time t by a predetermined constant.

These and other features, aspects, and advantages of the present invention will become better understood with reference to the following description and appended claims.

DESCRIPTION

Figure 1:
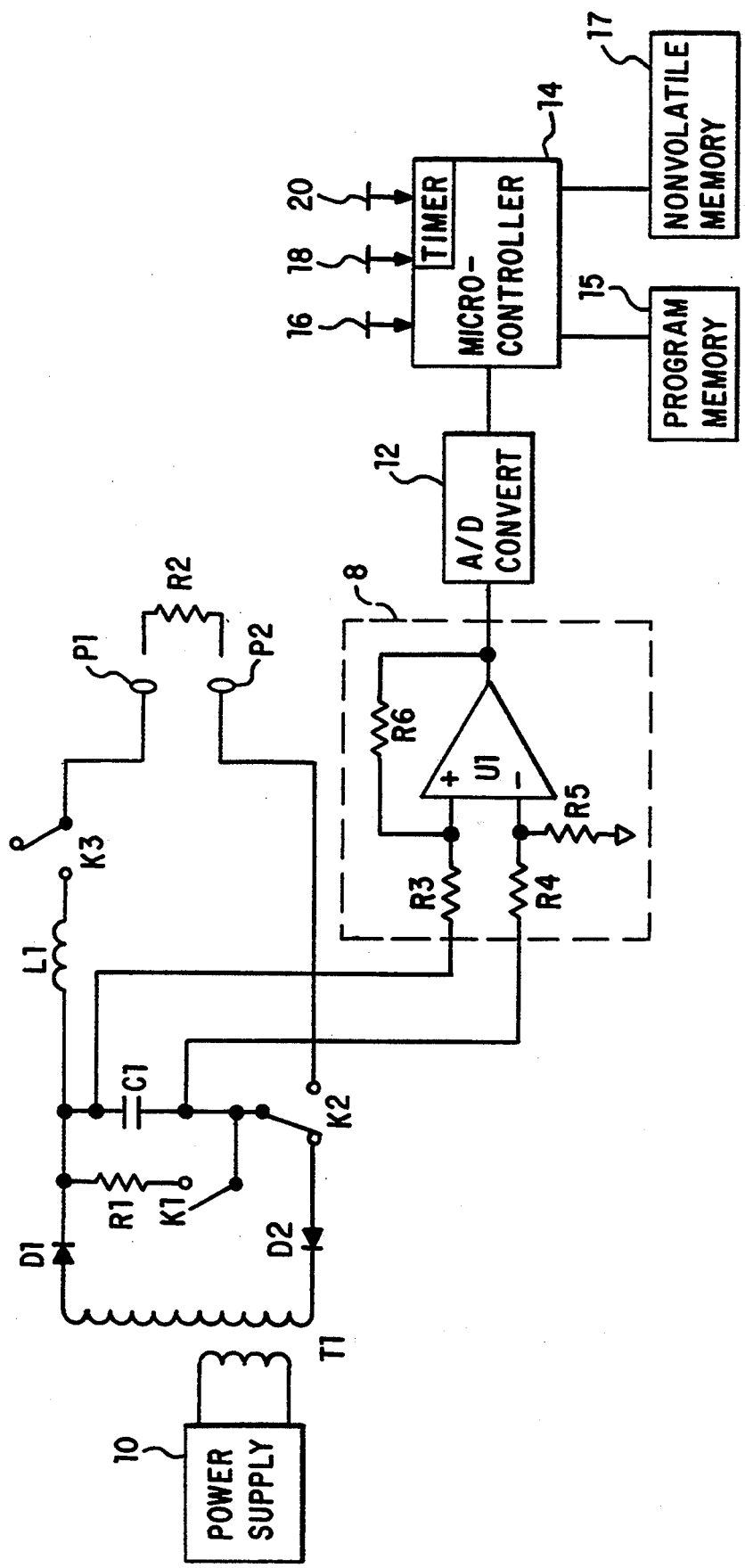
FIG. 1 shows a schematic diagram of a defibrillator capable of calibrating its storage capacitor.

Referring now to the drawings, a schematic diagram of a defibrillator is shown in FIG. 1. The primary coils of a transformer T1 connect to a pulsed-DC power supply 10. For a more detailed description of a pulsed-DC power supply, refer to a copending application Ser. No. 08/001,019 filed Jan. 6, 1993, now abandoned entitled "Improved Dual Voltage Power Supply," which is hereby incorporated by reference. The secondary coils of the transformer connect across a self healing capacitor C1 through two diodes D1 and D2 and a relay K2. The arrangement of the diodes allows a high voltage to be accumulated on the storage capacitor when the power supply is activated.

A safety resistor R1 and a safety relay K1 connected in series across the storage capacitor C1 allows the storage capacitor to be "disarmed" through the safety resistor R1. The safety relay K1 preferably is of the "normally closed" type, thus creating the default situation of preventing the storage capacitor from accumulating a charge. In FIG. 1, relays K2 and K3 are shown in their "charge" positions. FIG. 1 shows the relays in their "normally connected" positions. Relays K2 and K3 together form a double-pole double-throw relay. If semiconductor switching circuits are used for relays K2 and K3 in place of a double-pole double-throw mechanical relay, then their drives preferably are synchronized.

The energy accumulated on the storage capacitor C1 may be discharged into the patient (modeled in FIG. 1 by a resistor R2) through an inductor L1 and paddles P1 and P2. Discharge occurs when the relays K2 and K3 are moved to the positions opposite the positions they are shown in FIG. 1.

Four resistors R3, R4, R5, and R6 and an operational amplifier U1 form an instrumentation amplifier 8. The instrumentation amplifier has as its input the voltage across the storage capacitor C1. The output of the instrumentation amplifier 8 is supplied to an analog-to-digital (A/D) converter 12. The digital output of the A/D converter is provided to a microcontroller 14.

The microcontroller 14 executes program instructions contained in a program memory 15 and uses data stored in a nonvolatile memory 17. In executing the program instructions, the microcontroller controls the operation of the defibrillator, including the positions of the three relays K1, K2, and K3 and the activation of the power supply 10.

The microcontroller 14 accepts input from three switches: a "charge" switch 16, a "discharge" switch 18, and a "calibrate" switch 20. Through these switches, the operator commands the microcontroller to prepare the defibrillator for use, to discharge the storage capacitor C1 to the paddles P1 and P2, and to calibrate the storage capacitor. Alternatively, the "calibrate" switch could be a function key having different uses depending on the current operating mode. Only in the appropriate mode would the function key have the effect of initiating the calibration procedure.

Figure 3:
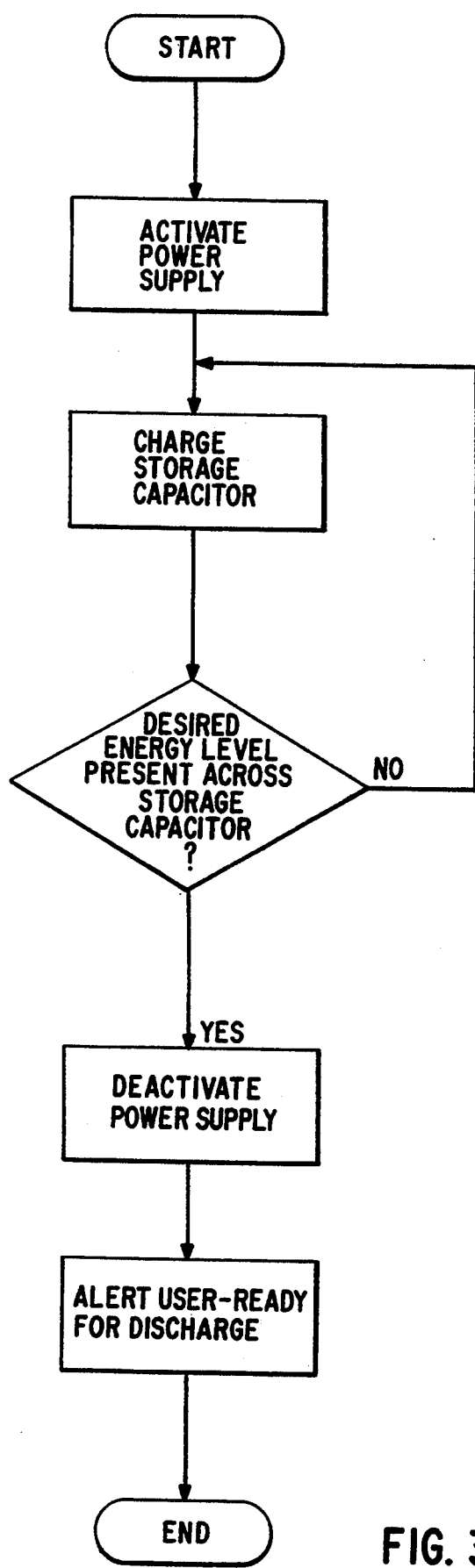
FIG. 3 shows a flow diagram for charging a defibrillator's storage capacitor.

During normal operation of the defibrillator, an operator activates the "charge" switch 16. In response, as shown in FIG. 3, the microcontroller 14 activates the power supply 10. The relays K1, K2, and K3 would already be in the positions shown in FIG. 1. The microcontroller then monitors the output of the A/D converter 12 until the storage capacitor C1 has a voltage corresponding to the desired discharge energy. At that time, the microcontroller deactivates the power supply and alerts the user that the defibrillator is ready for discharge.

Figure 4:
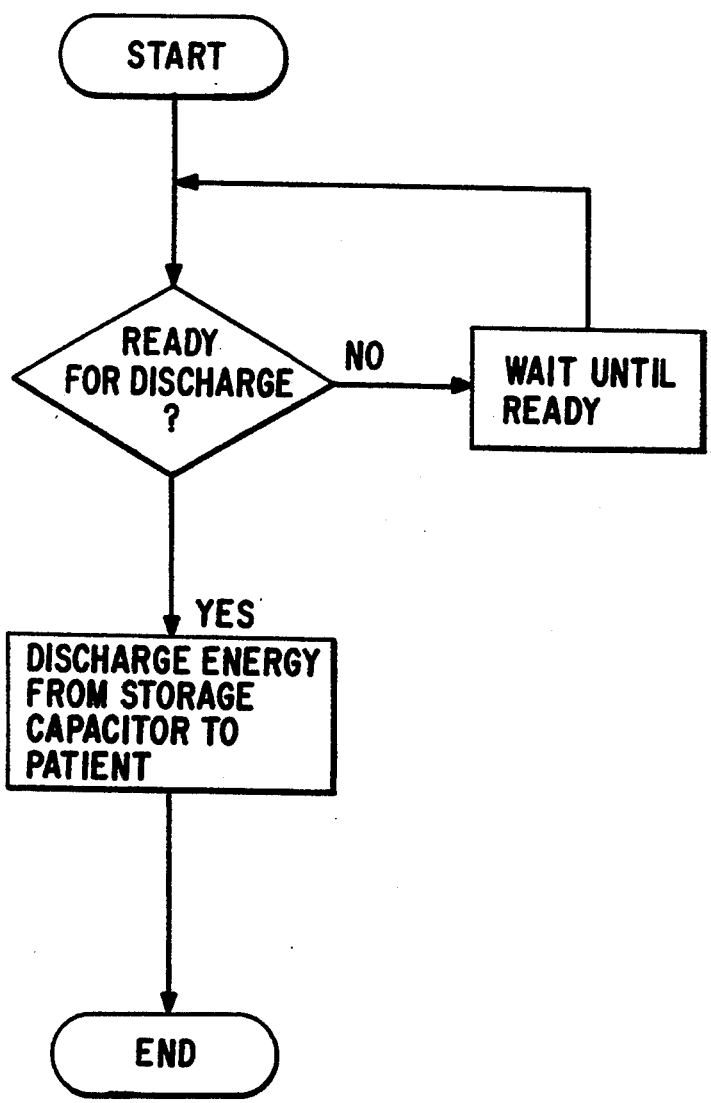
FIG. 4 shows a flow diagram for discharging a defibrillator's storage capacitor.

When the operator then activates the "discharge" switch 18 (typically a pair of switches, one on each paddle), as shown in FIG. 4 the microcontroller 14 moves relays K2 and K3 to cause the storage capacitor C1 to discharge through the patient R2. After approximately 300 milliseconds, the microcontroller returns the relays K2 and K3 to the positions shown in FIG. 1. Safety relay K1 preferably is closed concurrently with discharge.

To cause the defibrillator to determine the actual capacitance of the storage capacitor C1, the operator activates the "calibrate" switch 20. In response the microcontroller 14 activates the power supply 10, thereby causing the storage capacitor C1 to accumulate a charge. The relays K1, K2, and K3 remain in their default positions as shown in FIG. 1.

Meanwhile, the microcontroller 14 monitors the output of the A/D converter 12 until the capacitor C1 has a voltage greater than a first predetermined voltage $V_0$. At that time, the microcontroller deactivates the power supply 10 and closes the safety relay K1, causing the storage capacitor C1 to disarm through the safety resistor R1. During disarm, the microcontroller both monitors the output of the A/D converter until the storage capacitor reaches a second predetermined voltage $V_1$ and keeps track of elapsed time t.

The voltage V(t) on the storage capacitor C1 having capacitance C during disarm through resistor R1 as a function of time t can be described by the equation:

$$V(t) = V_0 e(-t/RC) \tag{3}$$

where $V_0$ is the voltage on the storage capacitor C1 at time t=0.

Solving equation (3) for C results in $$C = \frac{-t}{R} \cdot \frac{1}{\ln V(t) - \ln V_0}, \tag{4}$$

which can be simplified as $$C = \frac{t}{R(\ln(V_0/V_1))} \tag{5}$$

where $V_1$ is the voltage at an arbitrary time t.

All of the values on the right side of equation (5) are known after disarm, allowing the microcontroller 14 to calculate the capacitance C of the storage capacitor C1. Preferably, resistor R1 is known within one percent of its actual value.

By preselecting the starting and ending storage capacitor voltages, the microcontroller 14 can be spared from performing much of the calculations of equation (5). For example, by selecting the starting voltage $V_0$ to be 4500 Volts, the ending voltage $V_1$ to be 1960 Volts, and using the known value of resistance R as 47 kilo-Ohms, equation (5) simplifies to:

$$C = (2.56 \times 10^{-5})t. \tag{6}$$

By way of example, using equation (6) and a capacitance C of 34.5 micro-Farads yields an approximate decay time t of 1.35 seconds.

Figure 2:
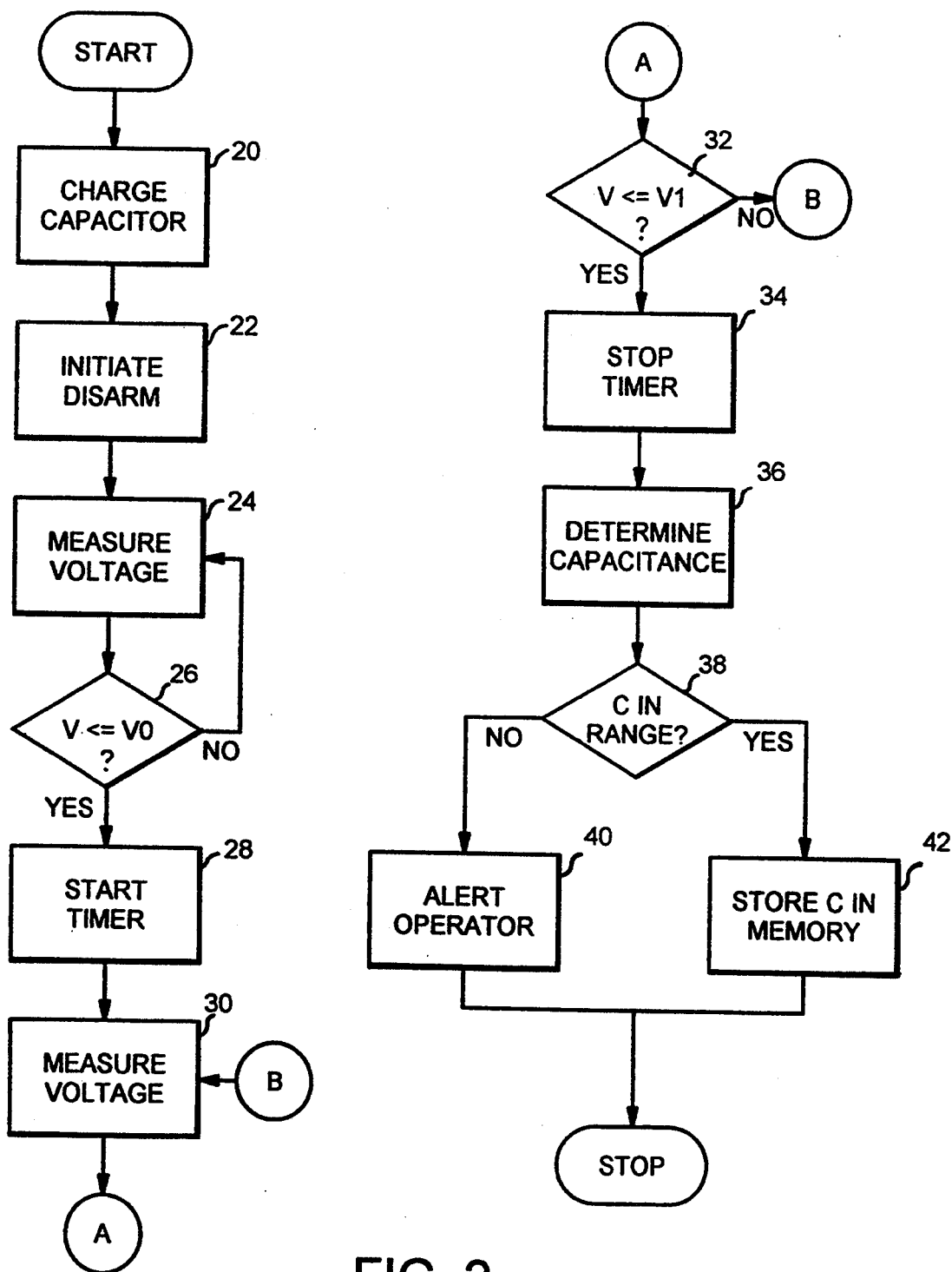
FIG. 2 shows a flow diagram for calibrating a defibrillator's storage capacitor.

Referring now to FIG. 2, a flow diagram for calibrating a defibrillator's storage capacitor is shown. As a first step, the storage capacitor C1 is charged 20 to a voltage greater than a first predetermined voltage $V_0$. The microcontroller 14 then initiates 22 the disarm of the storage capacitor C1 through the safety resistor R1. During disarm, the microcontroller measures 24 the voltage across the storage capacitor, comparing 26 it with the starting voltage $V_0$. If the measured voltage is less than or equal to the starting voltage $V_0$, the microcontroller starts 28 a timer contained in microcontroller 14. Otherwise, the microcontroller repeats the measuring and comparing steps of blocks 24 and 26.

After starting 28 the timer, the microcontroller 14 again measures 30 the voltage across the storage capacitor C1, comparing 32 it with a predetermined ending voltage $V_1$. If the measured voltage is less than or equal to the ending voltage $V_1$, the microcontroller stops 34 the timer. Otherwise, the microcontroller repeats the measuring and comparing steps of blocks 30 and 32.

Once the microcontroller 14 has determined the elapsed time t, the microcontroller determines 36 the capacitance C of the storage capacitor C1 using equation (5) or (6).

To ensure that no mistakes have been made, the microcontroller 14 compares 38 the newly determined capacitance C with the storage capacitor's nominal value. If the newly determined capacitance C is within an acceptable range of values, for example, within seven percent of the nominal value, then the microcontroller stores 42 the capacitance value in the nonvolatile memory 17 for use in future operations.

However, if the calculated value outside an acceptable range of values, then the microcontroller 14 signals 40 the operator that the calibration failed. The operator can then initiate another calibration sequence. If the capacitance of the capacitor C1 is indeed outside the acceptable range, subsequent calibration attempts will also result in calibration failure. In this manner, the operator is thus alerted to a hardware failure.

Thus, the present invention allows a defibrillator's storage capacitor to be calibrated as often as the operator desires. As a side benefit, the operator is assured that the capacitance is within the design limits of the defibrillator. No added elements are necessary in that the method uses the safety resistor and relay already present in the defibrillator. The instrumentation amplifier, the analog-to-digital converter 12, and microcontroller 14 are also present in the defibrillator.

What is claimed is:

1. A method of calibrating the energy output of a defibfillator having a self healing storage capacitor; a safety resistor connected in parallel with said self healing storage capacitor, and a microcontroller operatively coupled to said self healing storage capacitor, said method comprising the microcontroller executing steps of:
   receiving a calibration request;
   charging said self healing storage capacitor to a charging voltage greater than a starting voltage;
   discharging said self healing storage capacitor through said safety resistor;
   continuously measuring the voltage across said self healing storage capacitor as it discharges through said safety resistor;
   detecting, responsive to said measuring step, that the voltage across said self healing storage capacitor is less than or equal to said starting voltage;
   starting, responsive to said detecting step, a timer in said microcontroller;
   concluding, responsive to said measuring step, that said voltage across said self healing storage capacitor is leis than or equal to an ending voltage;
   stopping, responsive to said concluding step, said timer in said microcontroller;
   determining an elapsed time between a starting time of said timer in said starting step and an ending time of said timer in said stopping step;
   calculating a capacitance value of said self healing storage capacitor based on the starting voltage, the ending voltage, and the elapsed time; and
   storing said capacitance value of said self healing storage capacitor in a memory connected to said microcontroller for calibrating the energy output of said defibrillator.

2. The method of claim 1, further comprising the steps of
   receiving a charge request;
   charging said self healing storage capacitor until a voltage level sufficient to output a desired energy to a patient is present across said self healing storage capacitor;
   using said capacitance value of said self healing storage capacitor stored in said memory to assure that the self healing storage capacitor has been charged to said voltage level sufficient to output said desired energy to said patient.

3. The method of claim 2, further comprising the steps of:
   receiving a discharge request;
   discharging said desired energy to said patient.

4. The method of claim 1, wherein said storing step is responsive to the step of:
   verifying that said capacitance value is within a predetermined range.

5. A defibrillator having a self healing storage capacitor, a safety resistor connected in parallel with said self healing storage capacitor, and a microcontroller operatively coupled to said self healing storage capacitor, said microcontroller further comprising:
   means for receiving a calibration request;
   means for charging said self healing storage capacitor to a charging voltage greater than a starting voltage;
   means for discharging said self healing storage capacitor through said safety resistor;
   means for continuously measuring the voltage across said self healing storage capacitor as it discharges through said safety resistor;
   means for detecting, responsive to said measuring means, that the voltage across said self healing storage capacitor is less than or equal to said starting voltage;
   means for starting, responsive to said detecting means, a timer in said microcontroller;
   means for concluding, responsive to said measuring means, that said voltage across said self healing storage capacitor is less than or equal to an ending voltage;
   means for stopping, responsive to said concluding means, said timer in said microcontroller;
   means for determining an elapsed time between a starting time of said timer in said starting means and an ending time of said timer in said stopping means;
   means for calculating a capacitance value of said self healing storage capacitor based on the starting voltage, the ending voltage, and the elapsed time; and
   means for storing said capacitance value of said self healing storage capacitor in a memory connected to said microcontroller for calibrating the energy output of said defibrillator.

6. The defibrillator of claim 5, wherein the microcontroller further comprises:
   means for receiving a charge request;
   means for charging said self healing storage capacitor until a voltage level sufficient to output a desired energy to a patient is present across said self healing storage capacitor;
   means for using said capacitance value of said self healing storage capacitor stored in said memory to assure that the self healing storage capacitor has been charged to said voltage level sufficient to output said desired energy to said patient.

7. The defibrillator of claim 6, wherein the microcontroller, further comprises:
   means for receiving a discharge request; and
   means for discharging said desired energy to said patient.

8. The defibrillator of claim 5, wherein said means in said microcontroller for storing is responsive to means for verifying that said capacitance value is within a predetermined range.

* * * * *